United States Patent
Chadwick et al.

(10) Patent No.: US 10,660,847 B2
(45) Date of Patent: May 26, 2020

(54) COSMETIC COMPOSITIONS AND METHODS

(71) Applicant: MARY KAY INC., Addison, TX (US)

(72) Inventors: Edward Chadwick, Addison, TX (US); Geetha Kalahasti, Addison, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

(21) Appl. No.: 15/923,303

(22) Filed: Mar. 16, 2018

(65) Prior Publication Data

US 2018/0263894 A1    Sep. 20, 2018

Related U.S. Application Data

(60) Provisional application No. 62/472,636, filed on Mar. 17, 2017.

(51) Int. Cl.
| | | |
|---|---|---|
| *A61K 8/37* | (2006.01) | |
| *A61K 8/92* | (2006.01) | |
| *A61K 8/31* | (2006.01) | |
| *A61Q 19/00* | (2006.01) | |
| *A61Q 19/02* | (2006.01) | |
| *A61Q 19/08* | (2006.01) | |
| *A61Q 19/06* | (2006.01) | |
| *A61K 8/9789* | (2017.01) | |
| *A61K 8/73* | (2006.01) | |
| *A61K 8/60* | (2006.01) | |

(52) U.S. Cl.
CPC .............. *A61K 8/9789* (2017.08); *A61K 8/31* (2013.01); *A61K 8/37* (2013.01); *A61K 8/606* (2013.01); *A61K 8/735* (2013.01); *A61K 8/922* (2013.01); *A61Q 19/00* (2013.01); *A61Q 19/005* (2013.01); *A61Q 19/007* (2013.01); *A61Q 19/02* (2013.01); *A61Q 19/06* (2013.01); *A61Q 19/08* (2013.01); *A61K 2800/5922* (2013.01)

(58) Field of Classification Search
None
See application file for complete search history.

(56) References Cited

U.S. PATENT DOCUMENTS

| | | |
|---|---|---|
| 2,798,053 A | 7/1957 | Brown |
| 3,755,560 A | 8/1973 | Dickert et al. |
| 4,421,769 A | 12/1983 | Dixon et al. |
| 4,509,949 A | 4/1985 | Huang et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 4,883,659 A | 11/1989 | Goodman |
| 5,011,681 A | 4/1991 | Ciotti et al. |
| 5,087,445 A | 2/1992 | Haffey et al. |
| 5,100,660 A | 3/1992 | Hawe et al. |
| 7,615,657 B2 | 11/2009 | Bathurst et al. |
| 7,625,575 B2 | 12/2009 | Wagoner |
| 7,871,766 B2 | 1/2011 | Pauly et al. |
| 8,609,086 B2 | 12/2013 | Steward et al. |
| 8,623,386 B2 | 1/2014 | Schlossman et al. |
| 8,802,085 B2 | 8/2014 | Carter et al. |
| 2004/0109905 A1 | 6/2004 | Bagchi |
| 2005/0163880 A1 | 7/2005 | Pusateri et al. |
| 2008/0199489 A1 | 8/2008 | Parrinello |
| 2011/0305734 A1 | 12/2011 | Edelson et al. |
| 2013/0216596 A1 | 8/2013 | Viladot et al. |
| 2014/0341828 A1 | 11/2014 | Aratani et al. |
| 2015/0004139 A1 | 1/2015 | Lewis et al. |
| 2015/0044157 A1 | 2/2015 | Kulkarni et al. |
| 2015/0147360 A1 | 5/2015 | Levy |
| 2015/0342854 A1* | 12/2015 | Shibuya ................. A61Q 19/08 424/62 |

FOREIGN PATENT DOCUMENTS

| | | | |
|---|---|---|---|
| EP | 2561869 | 2/2013 | |
| LT | 6323 B | 10/2016 | |
| WO | 2010/149815 | 12/2010 | |
| WO | WO-2010149815 A1 * | 12/2010 | ............... A23D 9/00 |
| WO | 2013/149323 | 10/2013 | |
| WO | 2014/167557 | 10/2014 | |
| WO | WO 2014/195872 | 12/2014 | |
| WO | WO 2014/201541 | 12/2014 | |
| WO | WO-2015023926 A1 * | 2/2015 | ............... A61K 8/97 |
| WO | WO 2015/097185 | 7/2015 | |

OTHER PUBLICATIONS

Tash, "The complete list of comedogenic oils", pp. 1-41, 2016. (Year: 2016).*
Arnot, "How vegetables can give you that golden glow", [(retrieved from on-line website: https://www.theguardian.com/education/2011/feb/08/attractiveness-healthy-food, pp. 1-3, 2011)] (Year: 2011).*
Skin Inc., "Top tips for preventing and treating melasma," [(retrieved from on-line website: https://www.skininc.com/treatments/facial/brightening/Top-Tips-for-Preventing-and-Treating-Melasma-298167451.html, 2015 on-line publication)] (Year: 2015).*
WO-2010149815-A1 google english translation (Year: 2010).*
Tash, "The complete list of comedogenic oils", pp. 1-41,2016. (Year: 2016) (Year: 2016).*
Arnot, "How vegetables can give you that golden glow", [(retrieved from on-line website: https://www.theguardian.com/education/2011/feb/08/attractiveness-healthy-food, pp. 1-3, 2011)] (Year: 2011) (Year: 2011).*

(Continued)

*Primary Examiner* — Kyung S Chang
(74) *Attorney, Agent, or Firm* — Norton Rose Fulbright US LLP

(57) ABSTRACT

The present invention relates generally to methods of use and compositions useful for treating skin to reduce the appearance of wrinkles, moisturize skin, lighten skin, reduce inflammation, increase skin firmness, and/or increase skin elasticity. The composition includes a combination of *Persea gratissima* (avocado) oil, *Olea europaea* (olive) fruit oil, and *Argania spinosa* kernel oil.

12 Claims, No Drawings

(56) References Cited

OTHER PUBLICATIONS

Skin Inc., "Top tips for preventing and treating melasma," [(retrieved from on-line website: https://www.skininc.com/treatments/facial/brightening/Top-Tips-for-Preventing-and-Treating-Melasma-298167451 .html,2015 on-line publication)] (Year: 2015) (Year: 2015).*
WO-2010149815-A1 google english translation (Year: 2010) (Year: 2010).*
International Cosmetic Ingredient Dictionary and Handbook, Twelfth Edition, CTFA, vol. 1-2, 2008, pp. 60, 198, 365, 689, 733-734, 1351-1352, 1458, 1700-1702, 1981, 2529-2530.
Database GNPD Mintel: "Moist Crème Rich" Feb. 2017, XP002781543.
Database GNPD Mintel: "Complete in Gel Cream" Jan. 2017, XP002781544.
Database GNPD Mintel: "Wrinkle Reducing Night Cream" Oct. 2015, XP002781545.
International Search Report and Written Opinion issued for International Patent Application No. PCT/US2018/022790 dated Jun. 20, 2018, 15 pages.

\* cited by examiner

COSMETIC COMPOSITIONS AND METHODS

CROSS REFERENCE TO RELATED APPLICATIONS

The present application claims priority to U.S. Application 62/472,636 filed Mar. 16, 2017; the disclosure of which is hereby incorporated by reference in its entirety.

BACKGROUND OF THE INVENTION

A. Field of the Invention

The present invention relates generally to compositions that can be used in cosmetic compositions, used to clean, condition, and/or protect skin, and/or to improve the skin's condition and/or visual appearance. In certain aspects, the compositions can include, for example, a combination of ingredients to reduce the appearance of wrinkles, promote moisturization, lighten skin, reduce inflammation, increase skin firmness, and/or increase skin elasticity. This combination of ingredients can be included in a wide-range of product formulations (e.g., masks, serums, creams, cleansers, toners, gels, emulsions, gel emulsions, gel serums, etc.).

B. Description of Related Art

Ageing, chronic exposure to adverse environmental factors, malnutrition, fatigue, etc., can change the visual appearance, physical properties, or physiological functions of skin in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Maintaining moisture of the skin helps overcome some unwanted changes in skin. However, maintaining moisture of the skin can be difficult. Exposure to chemicals, solvents, washing, cosmetics, fabrics, or dry environments are some of the many ways that skin can lose moisture.

Moisturizers are complex mixtures of chemical agents specially designed to make the external layers of the skin (epidermis) softer and more pliable. Some moisturizers increase the skin's hydration (water content) by reducing evaporation. Naturally occurring skin lipids and sterols, as well as artificial or natural oils, humectants, emollients, lubricants, etc., may be part of the composition of commercial skin moisturizers. They usually are available as commercial products for cosmetic and therapeutic uses, but can also be made at home using common pharmacy ingredients. However, moisturizers are not perfect. Some problems associated with moisturizers include unpleasant tactile properties (e.g., heavy, greasy, or sticky feel), instability, skin-irritation, or insufficient moisturization capabilities.

Previous attempts to improve the visual appearance of skin with known skin active-ingredients have been shown to have various drawbacks such as skin irritation, prolonged recovery periods, or inefficient delivery of the promised skin benefits. Current products may not address each of these shortcomings.

SUMMARY OF THE INVENTION

The inventors have identified a solution to the problems associated with current cosmetic products. The solution resides in a combination of ingredients including *Persea gratissima* (avocado) oil, *Olea europaea* (olive) fruit oil, *Argania spinosa* kernel oil, jojoba esters, adenosine, sodium hyaluronate, and/or *Butyrospermum parkii* (shea butter), and optionally *Leptospermum scoparium* (manuka honey). This combination can be used to create topical skin compositions that reduce the appearance of wrinkles. In some instances, these combinations of ingredients provide moisture to the skin. In some instances, these combinations of ingredients prevent skin darkening, lighten dark spots, reduce melanin pigmentation, reduce inflammation, increase collagen production in skin to increase skin firmness and elasticity, increase elastin production in skin to resume skin shape, and/or increase laminin and fibronectin production to facilitate cellular adhesion of epidermal cells to the dermal-epidermal junction (DEJ). The inventors have further identified a solution to the problems associated with current cosmetic products that resides in a combination of ingredients including *Persea gratissima* (avocado) oil, *Olea europaea* (olive) fruit oil, *Argania spinosa* kernel oil, *Limnanthes alba* (meadowfoam) seed oil, hybrid sunflower oil, *Crambe abyssinica* seed oil, and optionally *Daucus carota* sativa (carrot) root extract. In some instances, these combinations of ingredients provide moisture to the skin. In some instances, these combinations of ingredients reduce the appearance of wrinkles. In some instances, these combinations of ingredients increase collagen production in the skin. In some instances, these combinations of ingredients increase elastin production in skin. In some instances, these combinations of ingredients increase laminin production in skin. In some instances, these combinations of ingredients increase fibronectin production in skin. In some instances, these combinations of ingredients inhibit B16 melanogenesis. In some instances, these combinations of ingredients inhibit tyrosinase expression. In some instances, these combinations of ingredients inhibit TNF-α expression.

In some aspects, there is disclosed a topical composition. In some aspects, the topical composition includes any one of, any combination of, or all of *Persea gratissima* (avocado) oil, *Olea europaea* (olive) fruit oil, *Argania spinosa* kernel oil, jojoba esters, adenosine, sodium hyaluronate, and *Butyrospermum parkii* (shea butter). In some instances, the topical composition includes an effective amount of *Persea gratissima* (avocado) oil, *Olea europaea* (olive) fruit oil, *Argania spinosa* kernel oil, jojoba esters, adenosine, sodium hyaluronate, and/or *Butyrospermum parkii* (shea butter) to reduce the appearance of wrinkles, and optionally *Leptospermum scoparium* (manuka honey). In some instances, the topical composition includes an effective amount of *Persea gratissima* (avocado) oil, *Olea europaea* (olive) fruit oil, *Argania spinosa* kernel oil, jojoba esters, adenosine, sodium hyaluronate, and/or *Butyrospermum parkii* (shea butter) to moisturize skin and/or reduce the appearance of wrinkles. In some instances, these combinations of ingredients increase collagen, elastin, fibronectin, and/or laminin production in skin. In some instances, these combinations of ingredients inhibit B16 melanogenesis and/or tyrosinase expression.

The amounts of the ingredients within the composition can vary (e.g., amounts can be as low as 0.000001% to as high as 98% w/w or any range therein). In some aspects, the topical composition includes 0.1 to 5% w/w of *Persea gratissima* (avocado) oil, 0.1 to 5% w/w of % w/w of *Olea europaea* (olive) fruit oil, 0.1 to 5% w/w of *Argania spinosa* kernel oil, 0.1 to 5% w/w of jojoba esters, 0.001 to 1% w/w of adenosine, 0.001 to 1% w/w of sodium hyaluronate, and/or 0.01 to 5% w/w of *Butyrospermum parkii* (shea butter).

In some instances, the topical composition includes water. In some instances, the composition includes 50 to 75% w/w of water. In some instances, the topical composition includes dicaprylyl carbonate; glycerin; cyclopentasiloxane; hydrogenated polyisobutene; arachidyl alcohol; ammonium acryloyldimethyltaurate/VP copolymer; and butylene glycol. In some instances, the topical composition includes 5 to 20% w/w of dicaprylyl carbonate; 1 to 10% w/w of glycerin; 0.1 to 5% w/w of cyclopentasiloxane; 0.1 to 5% w/w of hydrogenated polyisobutene; 0.01 to 3% w/w of arachidyl alcohol; 0.01 to 3% w/w of ammonium acryloyldimethyltaurate/VP copolymer; and 0.01 to 3% w/w of butylene glycol. In some instances, the topical composition is an emulsion, serum, gel, gel emulsion, or gel serum. In some instances, the topical composition is an oil in water emulsion or water in oil emulsion.

In some aspects, the topical composition includes any one of, any combination of, or all of *Persea gratissima* (avocado) oil, *Olea europaea* (olive) fruit oil, *Argania spinosa* kernel oil, *Limnanthes alba* (meadowfoam) seed oil, hybrid sunflower oil, *Crambe abyssinica* seed oil, and optionally *Daucus carota* sativa (carrot) root extract. In some instances, the topical composition includes an effective amount of *Persea gratissima* (avocado) oil, *Olea europaea* (olive) fruit oil, *Argania spinosa* kernel oil, *Limnanthes alba* (meadowfoam) seed oil, hybrid sunflower oil, *Crambe abyssinica* seed oil, and/or *Daucus carota* sativa (carrot) root extract to moisturize the skin. In some instances, these combinations of ingredients reduce the appearance of wrinkles, prevent skin darkening, lighten dark spots, reduce melanin pigmentation, reduce inflammation, increase skin firmness and elasticity, increase elastin production in skin to resume skin shape, and/or facilitate cellular adhesion of epidermal cells to the DEJ. In some instances, these combinations of ingredients increase collagen, elastin, fibronectin, and/or laminin production in skin. In some instances, these combinations of ingredients inhibit B16 melanogenesis and/or TNF-α expression. In some instances, the topical composition includes an effective amount of *Persea gratissima* (avocado) oil, *Olea europaea* (olive) fruit oil, *Argania spinosa* kernel oil, *Limnanthes alba* (meadowfoam) seed oil, hybrid sunflower oil, *Crambe abyssinica* seed oil, and/or *Daucus carota* sativa (carrot) root extract to reduce the appearance of wrinkles. In some instances, the topical composition includes an effective amount of *Persea gratissima* (avocado) oil, *Olea europaea* (olive) fruit oil, *Argania spinosa* kernel oil, *Limnanthes alba* (meadowfoam) seed oil, hybrid sunflower oil, *Crambe abyssinica* seed oil, and/or *Daucus carota* sativa (carrot) root extract to increase collagen, elastin, laminin, and/or fibronectin production in skin. In some instances, the topical composition includes an effective amount of *Persea gratissima* (avocado) oil, *Olea europaea* (olive) fruit oil, *Argania spinosa* kernel oil, *Limnanthes alba* (meadowfoam) seed oil, hybrid sunflower oil, *Crambe abyssinica* seed oil, and/or *Daucus carota* sativa (carrot) root extract to reduce inflammation of skin. In some instances, the topical composition includes an effective amount of *Persea gratissima* (avocado) oil, *Olea europaea* (olive) fruit oil, *Argania spinosa* kernel oil, *Limnanthes alba* (meadowfoam) seed oil, hybrid sunflower oil, *Crambe abyssinica* seed oil, and/or *Daucus carota* sativa (carrot) root extract. In some instances, the topical composition includes an effective amount of *Persea gratissima* (avocado) oil, *Olea europaea* (olive) fruit oil, *Argania spinosa* kernel oil, *Limnanthes alba* (meadowfoam) seed oil, hybrid sunflower oil, *Crambe abyssinica* seed oil, and/or *Daucus carota* sativa (carrot) root extract to prevent skin darkening and/or lighten dark spots on skin. In some instances, the topical composition includes an effective amount of *Daucus carota* sativa (carrot) root extract to increase collagen production in skin and/or inhibit B16 melanogenesis and/or TNF-α expression. In some instances, the topical composition includes an effective amount of *Argania spinosa* kernel oil to increase collagen production in skin for skin firming and elasticity and/or increase elastin production in skin to resume skin shape after stretching and/or increase laminin and/or fibronectin production in skin to facilitate cellular adhesion of epidermal cells to the DEJ.

The amounts of the ingredients within the composition can vary (e.g., amounts can be as low as 0.000001% to as high as 98% w/w or any range therein). In some aspects, the topical composition includes 0.1 to 5% w/w of *Persea gratissima* (avocado) oil, 0.1 to 5% w/w of *Olea europaea* (olive) fruit oil, 0.1 to 5% w/w of *Argania spinosa* kernel oil, 0.1 to 10% w/w of *Limnanthes alba* (meadowfoam) seed oil, 0.1 to 5% w/w of hybrid sunflower oil, 0.01 to 5% w/w of *Crambe abyssinica* seed oil, and/or 0.01 to 5% w/w of *Daucus carota* sativa (carrot) root extract.

In some instances, the topical composition includes water. In some instances, the composition includes 1 to 20% w/w of water. In some instances, the composition contains less than 10% water. In some instances, the composition is essentially anhydrous. In some instances, water is present in incidental amounts. In some instances, the topical composition includes mineral oil. In some instances, the composition contains 20 to 45% w/w of mineral oil. In some instances, the mineral oil is light mineral oil. In some instances, the composition contains 20 to 45% w/w of light mineral oil. In some instances, the composition contains PEG-20 glyceryl triisostearate. In some instances, the composition contains 5 to 30% w/w of PEG-20 glyceryl triisostearate. In some instances, the composition contains PEG-9 isostearate. In some instances, the composition contains 1 to 15% w/w of PEG-9 isostearate. In some instances, the composition contains butylene glycol, isononyl isononanoate, cetearyl ethylhexanoate, and polyethylene. In some instances, the composition contains 5 to 20% w/w of butylene glycol, 1 to 10% w/w of isononyl isononanoate, 0.1 to 10% w/w of cetearyl ethylhexanoate, and 0.1 to 10% w/w of polyethylene.

The topical compositions disclosed herein may further comprise one or more ingredients described herein. For example, the composition may comprise one or more additional ingredients selected from one or more conditioning agents, moisturizing agents, pH adjusters, structuring agents, inorganic salts, and preservatives. In some instances, the topical composition further includes water. In some instances, the topical compositions disclosed herein may exclude one or more ingredients described herein. For example, the composition may exclude one or more additional ingredients selected from one or more conditioning agents, moisturizing agents, pH adjusters, structuring agents, inorganic salts, and preservatives. In some instances, the composition may exclude one or more of *Persea gratissima* (avocado) oil, *Olea europaea* (olive) fruit oil, *Argania spinosa* kernel oil, jojoba esters, adenosine, sodium hyaluronate, *Butyrospermum parkii* (shea butter), *Limnanthes alba* (meadowfoam) seed oil, hybrid sunflower oil, *Crambe abyssinica* seed oil, *Daucus carota* sativa (carrot) root extract, and/or *Leptospermum scoparium* (manuka honey). In some instances, the topical composition excludes water. In some instances, the topical composition herein may be anhydrous or substantially anhydrous.

Methods of use for the compositions disclosed herein are also disclosed. In some aspects, a method is disclosed of improving a condition or appearance of skin, comprising applying any one of the compositions disclosed herein to skin in need thereof. In one aspect, any one of the compositions disclosed herein are applied to skin and the composition is left on the skin, or alternatively removed from the skin after a period of time.

In another aspect, the compositions disclosed herein are used to treat and/or reduce the appearance of wrinkles. In another aspect, the compositions disclosed here are used to treat and/or reduce the appearance of wrinkles by applying any one of the compositions disclosed herein to wrinkles, wherein the wrinkles are treated and/or the appearance of wrinkles are reduced. In another aspect, the compositions disclosed are used to prevent wrinkles comprising applying any one of the compositions disclosed herein to skin, wherein the wrinkles are prevented.

In another aspect, a method for increasing the production of collagen of skin is disclosed herein. In another aspect, a method for moisturizing skin is disclosed herein. In another aspect, a method for reducing the appearance of wrinkles is disclosed herein. In another aspect, a method for preventing skin darkening and lightening dark spots is disclosed herein. In another aspect, a method for reducing melanin pigmentation is disclosed herein. In another aspect, a method for reducing inflammation is disclosed herein. In another aspect, a method for increasing collagen production in skin to increase skin firmness and elasticity is disclosed herein. In another aspect, a method for increasing elastin production in skin to resume skin shape is disclosed herein. In another aspect, a method for increasing laminin and/or fibronectin production to facilitate cellular adhesion of epidermal cells to the DEJ is disclosed herein. In some aspects, the methods include applying any one of the topical compositions described herein to skin. In some aspects, the methods include applying the composition to a wrinkle.

In particular aspects, the compositions of the present invention are formulated as a topical skin composition. The composition can have a dermatologically acceptable vehicle or carrier for the compounds and extracts. The composition can further include a moisturizing agent or a humectant, a surfactant, a silicone containing compounds, a UV agent, an oil, and/or other ingredients identified in this specification or those known in the art. The composition can be a mask, lotion, cream, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, gel serums, gel emulsions, etc. The composition can be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include sodium benzoate, iodopropynyl butylcarbamate, methylparaben, propylparaben, or a mixture of methylparaben and propylparaben. In some embodiments, the composition is paraben-free.

Compositions of the present invention can have UVA and UVB absorption properties. The compositions can have a sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse off composition can be a skin cleanser, shampoo, conditioner, or soap. An example of a leave-on composition can be a skin moisturizer, sunscreen, mask, overnight cream, or a day cream.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a gel, a wash, a foundation, a night cream, a lipstick, a cleanser, a cleansing balm, a toner, a sunscreen, a mask, an anti-aging product, a deodorant, an antiperspirant, a perfume, a cologne, etc.

Also disclosed are the following Embodiments 1 to 30 of the present invention. Embodiment 1 is a method of treating skin to reduce the appearance of wrinkles, promote moisturization, lighten skin, reduce inflammation, increase skin firmness, and/or increase skin elasticity, the method comprising topically applying to the skin an effective amount of a topical composition comprising *Persea gratissima* (avocado) oil, *Olea europaea* (olive) fruit oil, and *Argania spinosa* kernel oil wherein the composition moisturizes the skin, reduces the appearance of wrinkles, reduces melanin secretion, inhibits TNF-α secretion, increases collagen production, increases elastin production, increases laminin, and/or increases fibronectin. Embodiment 2 is the method of Embodiment 1, wherein the topical composition further comprises an effective amount of jojoba esters, adenosine, sodium hyaluronate, and *Butyrospermum parkii* (shea butter). Embodiment 3 is the method of Embodiment 2, wherein the topical composition comprises 0.1 to 5% w/w of *Persea gratissima* (avocado) oil, 0.1 to 5% w/w of *Olea europaea* (olive) fruit oil, 0.1 to 5% w/w of *Argania spinosa* kernel oil, 0.1 to 5% w/w of jojoba esters, 0.001 to 1% w/w of adenosine, 0.001 to 1% w/w of sodium hyaluronate, and/or 0.01 to 5% w/w of *Butyrospermum parkii* (shea butter). Embodiment 4 is the method of any of Embodiments 1 to 3, wherein the topical composition further comprises water. Embodiment 5 is the method of Embodiment 4, wherein the topical composition comprises 50 to 75% w/w of water. Embodiment 6 is the method of Embodiment 1, wherein the topical composition further comprises an effective amount of *Limnanthes alba* (meadowfoam) seed oil, hybrid sunflower oil, and *Crambe abyssinica* seed oil. Embodiment 7 is the method of Embodiment 6, wherein the topical composition comprises 0.1 to 5% w/w of *Persea gratissima* (avocado) oil, 0.1 to 5% w/w of *Olea europaea* (olive) fruit oil, 0.1 to 5% w/w of *Argania spinosa* kernel oil, 0.1 to 10% w/w of *Limnanthes alba* (meadowfoam) seed oil, 0.1 to 5% w/w of hybrid sunflower oil, and 0.01 to 5% w/w of *Crambe abyssinica* seed oil. Embodiment 8 is the method of any of Embodiments 6 to 7, wherein the topical composition further comprises an effective amount of *Daucus carota* sativa (carrot) root extract to increase collagen production in skin, reduce inflammation in skin, and/or lighten skin. Embodiment 9 is the method of Embodiment 8, wherein the topical composition comprises 0.01 to 5% w/w of *Daucus carota* sativa (carrot) root extract. Embodiment 10 is the method of any of Embodiments 6 to 9, wherein the topical composition further comprises light mineral oil. Embodiment 11 is the method of Embodiment 10, wherein the topical composition comprises 20 to 45% w/w of light mineral oil. Embodiment 12 is the method of any of Embodiments 1 to 11, wherein the topical composition is an emulsion, serum, gel, gel emulsion, or gel serum. Embodiment 13 is the method of any of Embodiments 1 to 12, wherein the topical composition is an oil in water emulsion or a water in oil emulsion. Embodiment 14 is the method of any of Embodiments 1 to 13, wherein the effective amount of the topical composition reduces the appearance of wrinkles, promotes moisturization, lightens skin, reduces inflammation, increases skin firmness, and increases skin elasticity. Embodiment 15 is a topical composition comprising *Persea gratissima* (avocado) oil, *Olea europaea* (olive) fruit oil, and *Argania spinosa* kernel oil to reduce the appearance of wrinkles on skin, moisturize skin, decrease inflammation, increase skin firmness, increase elasticity, and/or lighten skin. Embodiment 16 is the topical composition of Embodiment 15, further comprising jojoba esters, adenosine, sodium hyaluronate, and *Butyrospermum parkii* (shea butter). Embodiment 17 is the topical composition of Embodiment 16, wherein the topical composition comprises an effective amount of *Persea gratissima* (avocado) oil, *Olea europaea* (olive) fruit oil, *Argania spinosa* kernel oil, jojoba esters, adenosine, sodium hyaluronate, and/or *Butyrospermum parkii* (shea butter) to reduce the appearance of wrinkles on skin and to moisturize skin. Embodiment 18 is the topical composition of any of Embodiments 15 to 17, comprising 0.1 to 5% w/w of *Persea gratissima* (avocado) oil, 0.1 to 5% w/w of % w/w of *Olea europaea* (olive) fruit oil, 0.1 to 5% w/w of *Argania spinosa* kernel oil, 0.1 to 5% w/w of jojoba esters, 0.001 to 1% w/w of adenosine, 0.001 to 1% w/w of sodium hyaluronate, and/or 0.01 to 5% w/w of *Butyrospermum parkii* (shea butter). Embodiment 19 is the topical composition of any of Embodiments 15 to 18, further comprising water. Embodiment 20 is the topical composition of Embodiment 19, comprising 50 to 75% w/w of water. Embodiment 21 is the topical composition of Embodiment 15, further comprising *Limnanthes alba* (meadowfoam) seed oil, hybrid sunflower oil, and *Crambe abyssinica* seed oil. Embodiment 22 is the topical composition of Embodiment 21, wherein the topical composition comprises an effective amount of *Persea gratissima* (avocado) oil, *Olea europaea* (olive) fruit oil, *Argania spinosa* kernel oil, *Limnanthes alba* (meadowfoam) seed oil, hybrid sunflower oil, and *Crambe abyssinica* seed oil to moisturize skin and/or reduce the appearance of wrinkles on skin. Embodiment 23 is the topical composition of any of Embodiments 21 to 22, comprising 0.1 to 5% w/w of *Persea gratissima* (avocado) oil, 0.1 to 5% w/w of *Olea europaea* (olive) fruit oil, 0.1 to 5% w/w of *Argania spinosa* kernel oil, 0.1 to 10% w/w of *Limnanthes alba* (meadowfoam) seed oil, 0.1 to 5% w/w of hybrid sunflower oil, and 0.01 to 5% w/w of *Crambe abyssinica* seed oil. Embodiment 24 is the topical composition of any of Embodiments 21 to 23, further comprising *Daucus carota* sativa (carrot) root extract. Embodiment 25 is the topical composition of Embodiment 24, wherein the topical composition comprises an effective amount of *Daucus carota* sativa (carrot) root extract to increase collagen production in skin, reduce inflammation in skin, and/or lighten skin. Embodiment 26 is the topical composition of any of Embodiments 24 to 25, comprising 0.01 to 5% w/w of *Daucus carota* sativa (carrot) root extract. Embodiment 27 is the topical composition of any of Embodiments 21 to 26, further comprising light mineral oil. Embodiment 28 is the topical composition of Embodiment 27, comprising 20 to 45% w/w of light mineral oil. Embodiment 29 is the topical composition of any of Embodiments 15 to 28, wherein the topical composition is an emulsion, serum, gel, gel emulsion, or gel serum. Embodiment 30 is the topical composition of any of Embodiments 15 to 29, wherein the topical composition is an oil in water emulsion or water in oil emulsion.

"Topical application" means to apply or spread a composition onto the surface of lips or keratinous tissue. "Topical skin composition" includes compositions suitable for topical application on skin and/or keratinous tissue. Such compositions are typically dermatologically-acceptable in that they do not have undue toxicity, incompatibility, instability, allergic response, and the like, when applied to skin and/or keratinous tissue. Topical skin care compositions of the present invention can have a selected viscosity to avoid significant dripping or pooling after application to skin and/or keratinous tissue.

"Keratinous tissue" includes keratin-containing layers disposed as the outermost protective covering of mammals and includes, but is not limited to, lips, skin, hair, and nails.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations refer to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the phrase "consisting essentially of," a basic and novel property of the compositions and methods of the present invention is the ability to reduce the appearance of wrinkles, increase collagen production in the skin, moisturize the skin, prevent skin darkening, lighten dark spots on skin, reduce melanin pigmentation, reduce inflammation, increase skin firmness and elasticity, help maintain skin shape, and/or facilitate cellular adhesion of epidermal cells to the DEJ.

The phrase "and/or" means and or or. To illustrate, A, B, and/or C includes: A alone, B alone, C alone, a combination of A and B, a combination of A and C, a combination of B and C, or a combination of A, B, and C. In other words, "and/or" operates as an inclusive or.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

As noted above, several of the unique aspects of the present invention are to combine in a topical cosmetic composition *Persea gratissima* (avocado) oil, *Olea europaea* (olive) fruit oil, *Argania spinosa* kernel oil, jojoba esters, adenosine, sodium hyaluronate, and/or *Butyrospermum parkii* (shea butter) and optionally *Leptospermum scoparium* (manuka honey). This allows for the benefits of reducing the appearance of wrinkles, promoting moisturization, preventing skin darkening, aiding to lighten dark spots, reducing melanin pigmentation, increasing collagen production in skin to increase skin firmness and elasticity, increasing elastin production in skin to resume skin shape, and/or increasing laminin and fibronectin production to facilitate cellular adhesion of epidermal cells to the DEJ. Further, several of the unique aspects of the present invention are to combine in a topical cosmetic composition *Persea gratissima* (avocado) oil, *Olea europaea* (olive) fruit oil, *Argania spinosa* kernel oil, *Limnanthes alba* (meadowfoam) seed oil, hybrid sunflower oil, *Crambe abyssinica* seed oil, and optionally *Daucus carota* sativa (carrot) root extract. This allows for the benefits of reducing the appearance of wrinkles, promoting moisturization, preventing skin darkening, aiding to lighten dark spots, reducing inflammation, increasing collagen production in skin to increase skin firmness and elasticity, increasing elastin production in skin to resume skin shape, and/or increasing laminin and fibronectin production to facilitate cellular adhesion of epidermal cells to the DEJ.

The following subsections describe non-limiting aspects of the present invention in further detail.

A particular composition of the present invention is designed to work as a topical composition. The composition relies on a unique combination of any one of, any combination of, or all of *Persea gratissima* (avocado) oil, *Olea europaea* (olive) fruit oil, *Argania spinosa* kernel oil, jojoba esters, adenosine, sodium hyaluronate, and/or *Butyrospermum parkii* (shea butter) or a unique combination of any one of, any combination of, or all of *Persea gratissima* (avocado) oil, *Olea europaea* (olive) fruit oil, *Argania spinosa* kernel oil, *Limnanthes alba* (meadowfoam) seed oil, hybrid sunflower oil, *Crambe abyssinica* seed oil, and optionally *Daucus carota* sativa (carrot) root extract. Non-limiting examples of such compositions are provided in Example 1, Table 1 and Table 2.

Some compositions disclosed herein can be applied to the skin and remain on the skin for a period of time (e.g., at least 1, 2, 3, 4, 5, 10, 20, 30, or 60 minutes or more). After which, the composition, if needed, can be rinsed from the skin or peeled from the skin. Some compositions disclosed herein can be applied to the skin and immediately rinsed from the skin. Some compositions disclosed herein can be applied to the skin and absorbed at least in part by the skin.

These and other non-limiting aspects of the present invention are described in the following sections.

A. Active Ingredients

The present invention is premised on a determination that a combination of active ingredients—*Persea gratissima* (avocado) oil, *Olea europaea* (olive) fruit oil, *Argania spinosa* kernel oil, jojoba esters, adenosine, sodium hyaluronate, and/or *Butyrospermum parkii* (shea butter) or *Persea gratissima* (avocado) oil, *Olea europaea* (olive) fruit oil, *Argania spinosa* kernel oil, *Limnanthes alba* (meadowfoam) seed oil, hybrid sunflower oil, *Crambe abyssinica* seed oil, and optionally *Daucus carota* sativa (carrot) root extract and/or *Leptospermum scoparium* (manuka honey)—can be used to reduce the appearance of wrinkles, promote moisturization, prevent skin darkening, lighten dark spots, reduce melanin pigmentation, reduce inflammation, increase collagen production in skin to increase skin firmness and elasticity, increase elastin production in skin to resume skin shape, and/or increase laminin and fibronectin production to facilitate cellular adhesion of epidermal cells to the DEJ.

This combination of ingredients can be used in different products to treat various skin conditions. By way of non-limiting examples, the combination of ingredients can be formulated in a mask, emulsion (e.g. oil in water, water in oil), a gel, a serum, a gel emulsion, a gel serum, a lotion, or a body butter.

*Persea gratissima* oil is an oil from the *Persea gratissima* plant, also known as avocado. In some instances, *Persea gratissima* oil is commercially available. In some instances, *Persea gratissima* oil can be supplied by Arista.

*Olea europaea* fruit oil is an oil from the fruit of an *Olea europaea* tree, also known as an olive tree. In some instances, *Olea europaea* fruit oil is commercially available. In some instances, *Olea europaea* fruit oil can be supplied by Lipo Chemicals.

*Argania spinosa* kernel oil is derived from the kernel of the fruit of the Argan tree, which is native to southern Morocco, the oil provides an anti-ageing effect and nourishes dry skin. In some instances, *Argania spinosa* kernel oil is commercially available. In some instances, *Argania spinosa* kernel oil can be supplied by Sophim under the tradename Seppic. In some instances, *Argania spinose* kernel oil can be supplied by BASF under the tradename Lipofructyl Argan LS 9779.

Jojoba esters are esters made from esterification of jojoba oil. In some instances, jojoba esters are commercially available.

Adenosine is a purine nucleoside comprising a molecule of adenine attached to a ribose sugar molecule moiety. Adenosine penetrates deeply into the skin to help prevent wrinkles and reduce UVB sun damage. In some instances, adenosine is commercially available.

Sodium hyaluronate is the sodium salt of hyaluronic acid, a compound that occurs naturally in various tissues including connective tissue. In some instances, sodium hyaluronate is commercially available.

*Butyrospermum parkii* (shea butter) is a slightly yellowish or ivory colored natural fat extracted from the seed of the African shea tree, *Butyrospermum parkii*. It is can be used as a moisturizer and salve. In some instances, *Butyrospermum parkii* (shea butter) is commercially available. In some instances, *Butyrospermum parkii* (shea butter) can be supplied by HallStar Company under the tradename Shea Butter—Ultra Refined.

*Limnanthes alba* (meadowfoam) seed oil is oil from the seed of *Limnanthes alba*, also known as meadowfoam or white meadowfoam. *Limnanthes alba* is a flowering plant native to California and Oregon. In some instances, *Limnanthes alba* (meadowfoam) seed oil is commercially available. In some instances, *Limnanthes alba* (meadowfoam) seed oil can be supplied by Fanning Corp.

Hybrid sunflower oil is and oil from hybrid sunflowers, also known as *Helianthus*. In some instances, hybrid sunflower oil is commercially available. In some instances, hybrid sunflower oil can be supplied by Floratech, USA.

*Crambe abyssinica* seed oil is an oil from the seed of *Crambe abyssinica*, a flowering plant that is native to the Mediterranean area. In some instances, *Crambe abyssinica* seed oil is commercially available. In some instances, *Crambe abyssinica* seed oil can be supplied by Desert Whale Jojoba Company/Vantage Specialty Chemicals.

*Daucus carota* sativa root extract is an extract from the root of *Daucus carota* sativa, a domesticated root vegetable also known as carrot. In some instances, *Daucus carota* sativa root extract is commercially available. In some instances, *Daucus carota* sativa root extract can be supplied by Southern Cross. In some instances, *Daucus carota* sativa root extract can be supplied by Abacross. In some instances, *Daucus carota* sativa root extract is a glycerol extract.

*Leptospermum scoparium* (manuka honey) is produced from the manuka or tea tree (*Leptospermum scoparium*). In some instances, *Leptospermum scoparium* (manuka honey) is commercially available. In some instances, *Leptospermum scoparium* (manuka honey) can be supplied by Abacross.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of any ingredient within the compositions can vary. In non-limiting embodiments, for example, the compositions can comprise, consist essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, peels, and ointments. Variations and other structures will be apparent to the skilled artisan and are appropriate for use in the present invention.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., Aloe vera, chamomile, cucumber extract, Ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate (octinoxate), isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, saccharide isomerate, sodium glucuronate, sodium PCA, sorbitol, sucrose, trehalose, urea, and xylitol.

Other examples include acetylated lanolin, acetylated lanolin alcohol, threonine, lysine, alanine, algae extract, *Aloe barbadensis, Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota* sativa) oil, castor (*Ricinus communis*) oil, ceramides, ceresin, ceteareth-5, ceteareth-12, ceteareth-20, cetearyl ethylhexanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, proline, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (Glycine soja) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (Triticum vulgare) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCL, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, hydroxypropyl cyclodextrin, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, cyclohexasiloxane, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Exfoliating Agent

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, alpha hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyl-taurate/vp copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerythritol (e.g., CARBOPOL™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Formulations having the ingredients disclosed herein were prepared as topical skin compositions. In some instances, the topical skin compositions can be prepared as an emulsion, serum, gel, gel emulsion, or gel serum. The formulation in Table 1 is an example of a topical skin composition prepared as an oil in water emulsion cream. The formulation in Table 2 is an example of a topical skin composition prepared as a water in oil emulsion cleanser.

TABLE 1^

| Ingredient | % Concentration (by weight) |
| --- | --- |
| Water | 64 |
| Dicaprylyl Carbonate | 8 |
| Glycerin | 3 |
| Cyclopentasiloxane | 2 |
| Hydrogenated polyisobutene | 2 |
| *Persea Gratissima* (avocado) oil | 2 |
| Jojoba esters | 2 |
| Arachidyl alcohol | 1 |
| Ammonium Acryloyldimethyltaurate/VP Copolymer | 1 |
| *Argania spinosa* kernel oil | 1 |
| Butylene glycol | 1 |
| *Olea europaea* (olive) fruit oil | 1 |
| *Leptospermum scoparium* (manuka honey) (optional) | 0.000001 to 10 |
| Betaine | 0.8 |
| Behenyl alcohol | 0.8 |
| Glyceryl stearate | 0.6 |
| Phenoxyethanol | 0.5 |
| Cetearyl alcohol | 0.5 |

TABLE 1^-continued

| Ingredient | % Concentration (by weight) |
| --- | --- |
| *Butyrospermum parkii* (shea) butter | 0.5 |
| Caprylyl glycol | 0.4 |
| PEG-100 stearate | 0.4 |
| Arachidyl glucoside | 0.4 |
| Sodium PCA | 0.3 |
| Tocopheryl acetate | 0.2 |
| Sorbitol | 0.2 |
| Polyacrylate-13 | 0.2 |
| Dimethicone | 0.2 |
| Xanthan gum | 0.1 |
| Disodium EDTA | 0.1 |
| Adenosine | 0.1 |
| Sodium hyaluronate | 0.02 |
| Excipients* | q.s. |

^Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*Excipients can be added, for example, to modify the rheological properties of the composition. Alternatively, the amount of water can be varied so long as the amount of water in the composition is at least 40% w/w, and preferably between 50 to 75% w/w.

TABLE 2^

| Ingredient | % Concentration (by weight) |
| --- | --- |
| Mineral oil, light | 33 |
| PEG-20 glyceryl triisostearate | 15 |
| Butylene glycol | 10 |
| PEG-9 isostearate (optional) | 8 |
| Water | 8 |
| Isononyl isononanoate | 5 |
| Cetearyl ethylhexanoate | 3 |
| *Limnanthes alba* (meadowfoam) seed oil | 3 |
| Polyethylene | 3 |
| *Argania spinosa* kernel oil | 2 |
| *Olea europaea* (olive) fruit oil | 2 |
| *Persea gratissima* (avocado) oil | 2 |
| *Helianthus Annuus* (sunflower) seed oil | 2 |
| *Crambe abyssinica* seed oil | 1 |
| *Daucus carota* sativa (carrot) root extract (optional) | 1 |
| Phenoxyethanol | 0.8 |
| Trihydroxystearin | 0.8 |
| Tocopheryl acetate | 0.3 |
| Excipients* | q.s. |

^Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*Excipients can be added, for example, to modify the rheological properties of the composition. Alternatively, the amount of water can be varied so long as the amount of water in the composition is below at least 40% w/w, and preferably between 0.01 to 20% w/w.

Example 2

In Vitro Activities

It has been determined that a composition comprising *Persea gratissima* (avocado) oil, *Olea europaea* (olive) fruit oil, *Argania spinosa* kernel oil, *Limnanthes alba* (meadowfoam) seed oil, hybrid sunflower oil, *Crambe abyssinica* seed oil, *Leptospermum scoparium* (manuka honey), and/or *Daucus carota* sativa (carrot) root extract can increase the production of collagen that can help improve skin firmness and elasticity, reduce TNF-α expression which can reduce inflammation, and inhibit B16 melanogensis, which can prevent skin darkening and lighten dark spots, inhibit tyrosinase, increase elastin production, increase fibronectin production, and/or increase laminin production. A summary of quantitative results is found in Table 3 and the methods used to determine the properties of the ingredients are provided below.

TABLE 3

| Assay | Ingredient | Activity |
| --- | --- | --- |
| Inhibition of TNF-α expression | *Daucus carota* sativa (carrot) root extract (0.1%) (optional) | +78% |
| Inhibition of B16 melanogenesis | *Leptospermum scoparium* (manuka honey) (0.1%) (optional) | +31% |
| | *Daucus carota* sativa (carrot) root extract (0.1%) (optional) | +27% |
| Inhibition of mushroom tyrosinase | *Leptospermum scoparium* (manuka honey) (0.1%) (optional) | +55% |
| Increase of collagen | *Argania spinosa* kernel oil (0.1%) | +28% |
| | *Daucus carota* sativa (carrot) root extract (1%) (optional) | +22% |
| Increase of elastin | *Argania spinosa* kernel oil (0.1%) | +129% |
| Increase of fibronectin | *Argania spinosa* kernel oil (0.1%) | +22% |
| Increase of laminin | *Argania spinosa* kernel oil (0.1%) | +135% |

Collagen Stimulation Assay: Collagen is an extracellular matrix protein critical for skin structure. Increased synthesis of collagen helps improve skin firmness and elasticity. This bioassay was used to examine the effect of *Daucus carota* sativa (carrot) root extract on the production of procollagen peptide (a precursor to collagen) by human epidermal fibroblasts. The endpoint of this assay was a spectrophotometric measurement that reflected the presence of procollagen peptide and cellular viability. The assay employed the quantitative sandwich enzyme immunoassay technique whereby a monoclonal antibody specific for procollagen peptide was pre-coated onto a microplate. Standards and samples were pipetted into the wells and any procollagen peptide present was bound by the immobilized antibody. After washing away any unbound substances, an enzyme-linked polyclonal antibody specific for procollagen peptide was added to the wells. Following a wash to remove any unbound antibody-enzyme reagent, a substrate solution was added to the wells and color developed in proportion to the amount of procollagen peptide bound in the initial step. Color development was stopped and the intensity of the color at 450 nm was measured using a microplate reader.

For generation of samples and controls, subconfluent normal human adult epidermal fibroblasts (Cascade Biologics) were cultivated in standard DMEM growth medium with 10% fetal bovine serum (Mediatech) at 37° C. in 10% $CO_2$. The cells were treated with each of the tested ingredients and controls for 3 days. Following incubation, cell culture medium was collected and the amount of procollagen peptide secretion was quantified using the sandwich enzyme linked immuno-sorbant assay (ELISA) from Takara (# MK101) as explained above.

It was shown that *Daucus carota* sativa (carrot) root extract increased the production of collagen between 22.3% to 65%. Additionally, it was shown that *Argania spinosa* kernel oil increased the production of collagen by 28%.

B16 Pigmentation Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes were cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion was measured by absorbance at 405 nm and cellular viability was quantified. Specifically, it was shown that *Daucus carota* sativa (carrot) root extract inhibited B16 melanogenesis expression by 27%. Additionally, it was shown that *Leptospermum scoparium* (manuka honey) inhibited B16 melanogenesis expression by 31%.

Elastin Stimulation Assay: Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers were monitored in cultured human fibroblasts by staining of cultured human fibroblasts using immunofluorescent antibodies directed against elastin. Specifically, it was shown that *Argania spinosa* kernel oil increased elastin production by 129%.

Laminin and Fibronectin Stimulation Assay: Laminin and fibronectin are major proteins in the dermal-epidermal junction (DEJ) (also referred to as the basement membrane). The DEJ is located between the dermis and the epidermis and interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal cells to the DEJ. Laminin and fibronectin secretion was monitored by quantifying laminin and fibronectin in cell supernatants of cultured human fibroblasts treated for 3 days with culture medium with or without the test ingredient(s). Following incubation, laminin and fibronectin content was measured using immunofluorescent antibodies directed against each protein in an enzyme linked immuno-sorbant assay (ELISA). Measurements were normalized for cellular metabolic activity, as determined by bioconversion of 3-(4,5-dimethylthiazol-2-yl)-5-(3-carboxymethoxyphenyl)-2-(4-sulfophenyl)-2H-tetrazolium (MTS). Specifically, it was shown that *Argania spinosa* kernel oil increased fibronectin production by 22%, and increased laminin production by 135%.

Tumor Necrosis Factor Alpha (TNF-α) Assay: The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples were pipetted into the wells and any TNF-α present was bound by the immobilized antibody. After washing away any unbound substances, an enzyme-linked polyclonal antibody specific for TNF-α was added to the wells. Following a wash to remove any unbound antibody-enzyme reagent, a substrate solution was added to the wells and color developed in proportion to the amount of TNF-α bound in the initial step using a microplate reader for detection at 450 nm. The color development was stopped and the intensity of the color was measured. Sub-confluent normal human adult keratinocytes (Cascade Biologics) cultivated in EPILIFE™ standard growth medium (Cascade Biologics) at 37° C. in 5% $CO_2$, was treated with phorbol 12-myristate 13-acetate (PMA, 10 ng/ml, Sigma Chemical, # P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium was collected and the amount of TNF-α secretion quantified using a sandwich enzyme linked immuno-sorbant assay (ELISA) from R&D Systems (# DTA00C). Specifically, it was shown that *Daucus carota* sativa (carrot) root extract inhibited TNF-α expression by 78%.

Mushroom tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) was incubated with its substrate L-Dopa (Fisher) in the presence or absence of each of the active ingredients, any one of the combination of ingredients, or compositions having said combinations disclosed in the specification. Pigment formation was evaluated by colorimetric plate reading at 490 nm. The percent inhibition of mushroom tyrosinase activity was calculated compared to non-treated controls to determine the ability of test ingredients or combinations thereof to inhibit the activity of purified enzyme. Test extract inhibition was compared with that of kojic acid (Sigma). Specifically, it was shown that *Leptospermum scoparium* (manuka honey) inhibited mushroom tyrosinase expression by 55%.

Example 3

Additional Assays

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Antioxidant (AO) Assay: An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®+ metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Mich. USA) can be used as an in vitro bioassay to measure the total anti-oxidant capacity of each of any one of the active ingredients, combination of ingredients, or compositions having said combinations disclosed in the specification. The protocol can be followed according to manufacturer recommendations.

ORAC Assay: Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. Antioxidant activity indicates a capability to reduce oxidizing agents (oxidants). This assay quantifies the degree and length of time it takes to inhibit the action of an oxidizing agent, such as oxygen radicals, that are known to cause damage to cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; and commercially available kits such as Zen-Bio ORAC Antioxidant Assay kit (# AOX-2)). The Zen-Bio ORAC Antioxidant Assay kit measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner.

Matrix Metalloproteinase 3 and 9 Enzyme Activity (MMP3; MMP9) Assay: An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M-1 cm-1 at pH 6.0 and above 7). The active ingredients, any one of the combination of ingredients, or compositions having said combinations disclosed in the specification can be assayed.

Matrix Metalloproteinase 1 Enzyme Activity (MMP1) Assay: An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (# E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The Enz/Chek Gelatinase/Collagenase Assay kit (# E12055) from Invitrogen is designed as an in vitro assay to measure MMP1 enzymatic activity. The active ingredients, any one of the combination of ingredients, or compositions having said combinations disclosed in the specification can be assayed. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colorimetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygenase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachidonic acid may then be converted to hydroxyeicosotrienenoic (HETE) acid derivatives, that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and the mixtures can be incubated for an additional 10 min at room temperature. Colorimetric substrate can be added to terminate catalysis and color progression can be evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay: ENZCHEK® Elastase Assay (Kit # E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase when utilizing the EnzChek Elastase Assay Kit for screening for elastase inhibitors.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve.

This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Production of Filaggrin: Changes in the production of filaggrin in keratinocytes due to each of the active ingredients, any one of the combination of ingredients, or compositions having said combinations disclosed in the specification can be measured. Filaggrin is the precursor to Natural Moisturizing Factor (NMF) in the skin. Increased NMF increases the moisture content of the skin. Filaggrin production in treated and non-treated keratinocytes can be determined using a bioassay that analyzes filaggrin concentration in keratinocyte cell lysates. A non-limiting example of a bioassay that can be used to quantify filaggrin production is the PROTEINSIMPLE® SIMON™ western blotting protocol. For each sample, normal human epidermal keratinocytes (NHEK) are grown in EPI-200—Mattek EPILIFE™ growth media with calcium from Life Technologies (M-EP-500-CA). NHEK are incubated in growth medium overnight at 37° C. in 5% $CO_2$ prior to treatment. NHEK are then incubated in growth medium with 1% test compound/extract or no compound/extract (negative control) for 24 to 36 hours. The NHEK can then be washed, collected, and stored on ice or colder until lysed on ice using a lysis buffer and sonication. The protein concentrations of the samples can be determined and used to normalize the samples. The lysates can be stored at −80° C. until use in the quantification assay.

The PROTEINSIMPLE® SIMON™ western blotting bioassay assay employs a quantitative western blotting immunoassay technique using an antibody specific for filaggrin to quantitatively detect filaggrin in the test samples. Cell samples are lysed and normalized for protein concentration. Normalized samples and molecular weight standards can then be loaded and ran on a denatured protein separation gel using capillary electrophoresis. The proteins in the gel are immobilized and immunoprobed using a primary antibody specific for filaggrin. The immobilized proteins can then be immunoprobed with an enzyme-linked detection antibody that binds the primary antibody. A chemiluminescent substrate solution can then be added to the immobilized proteins to allow chemiluminescent development in proportion to the amount of filaggrin bound in the immobilization. The chemiluminescent development is stopped at a specific time and the intensity of the chemiluminescent signal can be measured and compared to positive and negative controls.

Production of Occludin: Changes in the production of occludin in keratinocytes due to each of the active ingredients, any one of the combination of ingredients, or compositions having said combinations disclosed in the specification can be measured. Occludin is a protein critical to the formulation of tight junctions and the skin's moisture barrier function. A non-limiting example of how occludin production in treated and non-treated keratinocytes can be determined is by the use of a bioassay that analyzes occludin concentration in keratinocyte cell lysates. The bioassay can be performed using PROTEINSIMPLE® SIMON™ western blotting protocol. For the samples, adult human epidermal keratinocytes (HEKa) from Life Technologies (C-005-5C) can be grown at 37° C. and 5% CO2 for 24 hours in EPILIFE™ growth media with calcium from Life Technologies (M-EP-500-CA) supplemented with Keratinocyte Growth Supplement (HKGS) from Life Technologies (S-101-5). HEKa are then incubated in growth medium with test compound/extract, no compound/extract for negative control, or with 1 mM $CaCl_2$ for positive control for 24 to 48 hours. The HEKa are then washed, collected, and stored on ice or colder until lysed on ice using a lysis buffer and sonication. The protein concentrations of the samples can be determined and used to normalize the samples. The lysates are stored at −80° C. until use in the bioassay.

The PROTEINSIMPLE® SIMON™ western blotting bioassay assay employs a quantitative western blotting immunoassay technique using an antibody specific for occludin to quantitatively detect occludin in the test samples. Cell samples are lysed and normalized for protein concentration. Normalized samples and molecular weight standards are then loaded and ran on a denatured protein separation gel using capillary electrophoresis. The proteins in the gel are then immobilized and immunoprobed using a primary antibody specific for occludin. The immobilized proteins are immunoprobed with an enzyme-linked detection antibody that binds the primary antibody. A chemiluminescent substrate solution is then added to the immobilized proteins to allow chemiluminescent development in proportion to the amount of occludin bound in the immobilization. The chemiluminescent development can be stopped at a specific time and the intensity of the chemiluminescent signal can be measured and compared to positive and negative controls.

Keratinocyte Monolayer Permeability: Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in EPILIFE™ growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample−Percent Permeability of untreated control.

Production of Hyaluronic Acid: Changes in the production of hyaluronic acid in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% $CO_2$ in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

Inhibition of Hyaluronidase Activity: Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol # EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity= (Inhibitor stopped wells absorbance at 600 nm−inhibitor reaction wells absorbance at 600 nm); Initial activity=control enzyme absorbance at 600 nm; Percent Inhibition=[(Initial activity/Inhibitor Activity)*100]−100.

Peroxisome Proliferator-Activated Receptor Gamma (PPAR-γ) Activity: Changes in the activity of PPAR-γ due to each of the active ingredients, any one of the combination of ingredients, or compositions having said combinations disclosed in the specification can be measured. PPAR-γ is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

Cytokine array: Human epidermal keratinocytes are cultured to 70-80% confluency. The media in the plate is aspirated and 0.025% trypsin/EDTA is added. When the cells became rounded, the culture dish is gently tapped to release the cells. The trypsin/EDTA containing cells are removed from the culture dish and neutralized. Cells are centrifuged for 5 min. at 180×g to form a pellet of cells. The supernatant is aspirated. The resulting pellet is resuspended in EPILIFE™ media (Cascade Biologics). The cells are seeded in 6-well plates at approximately 10-20% confluency. After the cells became approximately 80% confluent, the media is aspirated and 1.0 ml of EPILIFE™, along with phorbol 13-Myristate 12-acetate ("PMA") (a known inducer of inflammation) and the test composition dilutions are added to two replicate wells (i.e., 1.0% (100 µl of 100× stock) and 0.1% (10 µl of 100× stock) test compositions are diluted into a final volume of 1 ml EPILIFE™ Growth Medium). The media is gently swirled to ensure adequate mixing. In addition, 1.0 ml of EPILIFE™ is added to the control wells, with and without additional PMA. The plates are then incubated at 37±1° C. and 5.0±1% $CO_2$ for approximately 5 hours after dosing. Following this 5-hour incubation, all media is collected in conical tubes and frozen at −70° C.

For analysis, a 16-pad hybridization chamber is attached to 16-pad FAST slides arrayed in triplicate with 16 anticytokine antibodies plus experimental controls (Whatman BioSciences), and the slides are placed into a FASTFrame (4 slides per frame) for processing. Arrays are blocked for 15 min. at room temp. using 70 ml S&S Protein Array Blocking buffer (Whatman Schleicher and Scheull). Blocking buffer is removed and 70 ml of each supernatant sample is added to each array. Arrays are incubated for 3 hours at room temp. with gentle agitation. Arrays are washed 3 times with TBS-T. Arrays are treated with 70 ml of an antibody cocktail, containing one biotinylated antibody corresponding to each of the arrayed capture antibodies. Arrays are incubated for 1 hour at room temp. with gentle agitation. Arrays are washed 3 times with TBS-T. Arrays are incubated with 70 ml of a solution containing streptavidin-Cy5 conjugate for 1 hour at room temp. with gentle agitation. Arrays are washed 3 times with TBS-T, quickly rinsed in de-ionized water, and dried.

Slides can be imaged in a Perkin-Elmer ScanArray 4000 confocal fluorescent imaging system. Array images can be saved and analyzed using Imaging Research ArrayVision software. Briefly, spot intensities are determined by subtracting background signal. Spot replicates from each sample condition can be averaged and then compared to the appropriate controls.

Endothelial Tube Formation: Endothelial tube formation is involved in angiogenesis and micro-vessel capillary formation. Capillary formation and angiogenesis may contribute to redness and rosacea of the skin. The ability for endothelial cells to form tubes in the presence or absence of test extracts and compounds may be determined using a capillary tubule disruption assay with pre-formed primary human umbilical vein endothelial cells (HUVEC) in a cell culture system.

Briefly, HUVECs are cultured in vitro on Extracellular Matrix, which stimulates the attachment and tubular morphogenesis of endothelial cells to form capillary-like lumen structures. These in vitro formed capillary tubules are similar to human blood vessel capillaries in many aspects. The capillary tube assay is based on this phenomenon and is used for evaluation of potential vasculature targeting agents.

HUVEC cultures are grown in a 5% $CO_2$ 37° C. cell incubator. The full growth medium for HUVECs is Endothelial Cell Basal Medium (EBM) supplemented with 2% fetal bovine serum (FBS), 12 µg/ml bovine brain extract, 1 µg/ml hydrocortisone, and 1 µg/ml GA-1000 (gentamicin-amphothericin). HUVEC cultures between passage 3 and 8 may be used for all assay experiments.

HUVECs are pre-labeled with fluorescent agent Calcein AM and seeded in Extracellular Matrix coated 96-well culture plate with their full growth medium. After about four hours of the morphogenesis process, the endothelial capillary tubes should be formed. Then, test agent in designed doses in 50 µl volume is applied into the formed capillary tubule cultures as treatment conditions. The no-treatment controls can be added with vehicle of test agents. Sutent, a FDA approved anti-angiogenic drug one concentration can be included as assay performance control. After about six hours of treatment, the endothelial tubule morphology in each well is examined by microscopy, imaged, and the capillary disrupting activities under treatment conditions can be quantitatively analyzed. Each test conditions can be conducted in duplicate wells, including controls.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.
Cosmetic Ingredient Dictionary, Third Edition, CTFA, 1982
International Cosmetic Ingredient Dictionary, Fourth edition, CTFA, 1991
International Cosmetic Ingredient Dictionary and Handbook, Tenth Edition, CTFA, 2004
International Cosmetic Ingredient Dictionary and Handbook, Twelfth Edition, CTFA, 2008

The invention claimed is:

1. A method of treating skin to reduce the appearance of wrinkles, increase moisturization, lighten skin, reduce inflammation, increase skin elasticity, and/or increase skin firmness, the method comprising topically applying to the skin an effective amount of a topical composition comprising 0.1 to 5% w/w of *Persea gratissima* oil, 0.1 to 5% w/w of *Olea europaea* fruit oil, 0.1 to 5% w/w of *Argania spinosa* kernel oil, 0.1 to 5% w/w of jojoba esters, 0.001 to 1% w/w of adenosine, 0.001 to 1% w/w of sodium hyaluronate, 0.01 to 5% w/w of *Butyrospermum parkii* butter, 50 wt. % to 75 wt. % water, 3 wt. % to 12 wt. % dicaprylyl carbonate, 1 wt. % to 5 wt. % glycerin, 0.1 wt. % to 5 wt. % cyclopentasiloxane, 0.1 wt. % to 5 wt. % hydrogenated polyisobutene, 0.1 wt. % to 3 wt. % arachidyl alcohol, 0.1 wt. % to 3 wt. % ammonium acryloyldimethyltaurate/vinyl pyrrolidone (VP) copolymer, and 0.1 wt. % to 3 wt. % butylene glycol, wherein the composition reduces melanin secretion, inhibits TNF-α secretion, increases collagen production, increases elastin production, increases laminin production, and/or increases fibronectin production.

2. The method of claim 1, wherein the topical composition further comprises an effective amount of *Daucus carota* sativa root extract to increase collagen production in skin, reduce inflammation in skin, reduce melanin production, and/or lighten dark spots in skin.

3. The method of claim 2, wherein the topical composition comprises 0.01 to 5% w/w of *Daucus carota* sativa root extract.

4. The method of claim 1, wherein the topical composition is an emulsion, serum, gel, gel emulsion, or gel serum.

5. The method of claim 1, wherein the topical composition further comprises:

betaine;
behenyl alcohol;
glyceryl stearate;
phenoxyethanol;
cetearyl alcohol;
caprylyl glycol;
PEG-100 stearate;
arachidyl glucoside;
sodium pyroglutamic acid;
tocopheryl acetate;
sorbitol;
polyacrylate-13;
dimethicone;
xanthan gum; and
disodium EDTA.

6. The method of claim 5, wherein the topical composition comprises:
0.1 wt. % to 3 wt. % betaine;
0.1 wt. % to 3 wt. % behenyl alcohol;
0.1 wt. % to 3 wt. % glyceryl stearate;
0.1 wt. % to 3 wt. % phenoxyethanol;
0.1 wt. % to 3 wt. % cetearyl alcohol;
0.01 wt. % to 1.5 wt. % caprylyl glycol;
0.01 wt. % to 1.5 wt. % PEG-100 stearate;
0.01 wt. % to 1.5 wt. % arachidyl glucoside;
0.01 wt. % to 1.5 wt. % sodium pyroglutamic acid;
0.01 wt. % to 1 wt. % tocopheryl acetate;
0.01 wt. % to 1 wt. % sorbitol;
0.01 wt. % to 1 wt. % polyacrylate-13;
0.01 wt. % to 1 wt. % dimethicone;
0.01 wt. % to 1 wt. % xanthan gum; and
0.01 wt. % to 1 wt. % disodium EDTA.

7. The method of claim 1, wherein the topical composition further comprises 0.000001 wt. % to 10 wt. % *Leptospermum scoparium* honey.

8. A method of treating skin to reduce the appearance of wrinkles, increase moisturization, lighten skin, reduce inflammation, increase skin elasticity, and/or increase skin firmness, the method comprising topically applying to the skin an effective amount of a topical composition comprising: 0.1 to 5% w/w of *Persea gratissima* oil, 0.1 to 5% w/w of *Olea europaea* fruit oil, 0.1 to 5% w/w of *Argania spinosa* kernel oil, 0.1 to 10% w/w of *Limnanthes alba* seed oil, 0.1 to 5% w/w of hybrid sunflower oil, and 0.01 to 5% w/w of *Crambe abyssinica* seed oil, 20 to 45% w/w of light mineral oil, 3 wt. % to 12 wt. % water, 10 wt. % to 20 wt. % PEG-20 glyceryl triisostearate, 5 wt. % to 15 wt. % butylene glycol, 1 wt. % to 10 wt. % isononyl isononanoate, 1 wt. % to 5 wt. % cetearyl ethylhexanoate, and 1 wt. % to 5 wt. % polyethylene wherein the composition reduces melanin secretion, inhibits TNF-α secretion, increases collagen production, increases elastin production, increases laminin production, and/or increases fibronectin production.

9. The method of claim 8, wherein the topical composition further comprises:
phenoxyethanol;
trihydroxystearin; and
tocopheryl acetate.

10. The method of claim 9, wherein the topical composition comprises:
0.1 wt. % to 3 wt. % phenoxyethanol;
0.1 wt. % to 3 wt. % trihydroxystearin; and
0.01 wt. % to 1.5 wt. % tocopheryl acetate.

11. The method of claim 8, wherein the topical composition further comprises 3 wt. % to 12 wt. % PEG-9 isostearate.

12. The method of claim 8, wherein the topical composition is a water in oil emulsion cleanser and wherein topically applying the topical composition to the skin cleanses the skin.

* * * * *